United States Patent [19]

Gruber et al.

[11] 3,987,090

[45] Oct. 19, 1976

[54] HYDROXY ESTERS OF ACRYLIC AND METHACRYLIC ACIDS

[75] Inventors: Wilhelm Gruber; Hans Walter, both of Darmstadt, Germany

[73] Assignee: Rohm GmbH, Darmstadt, Germany

[22] Filed: Aug. 23, 1974

[21] Appl. No.: 499,987

[30] Foreign Application Priority Data

Sept. 8, 1973 Germany............................ 2345394

[52] U.S. Cl............................................. 260/486 B
[51] Int. Cl.².......................................... C07C 69/54
[58] Field of Search ................................ 260/486 B

[56] References Cited
UNITED STATES PATENTS
2,819,296    1/1958    Carnes ............................ 260/486 B

OTHER PUBLICATIONS

Shreibert et al., as cited in C. A. 68, 3227a, (1968).

Shreibert et al. II, as cited in C. A. 67, 73932, (1967).

Leplyunin et al., as cited in C. A. 78 98090, (1973).

Sechkovskaya et al., as cited in C. A. 74, 126145, (1971).

*Primary Examiner*—Paul J. Killos
*Attorney, Agent, or Firm*—Curtis, Morris & Safford

[57] ABSTRACT

An improvement is disclosed of a process for reacting acrylic or methacrylic acid with a vicinal epoxide in the presence of a basic nitrogen compound to produce the corresponding hydroxy ester which comprises carrying out the reaction in the presence of a compound of the formula R—($NO_2$) as stabilizer in which R is a linear or branched alkyl or alkenyl or from 1 to 18 carbon atoms.

11 Claims, No Drawings

HYDROXY ESTERS OF ACRYLIC AND METHACRYLIC ACIDS

This invention relates to an improvement in the preparation of hydroxy esters of acrylic- and methacrylic acids, more particularly in the preparation of 2-hydroxy alkyl esters of these acids.

It is known that such esters can be prepared by reacting acrylic- or methacrylic acid in the presence of basic nitrogen compounds as catalysts with 1,2-alkylene oxides. When this reaction is carried out at elevated temperatures, e.g. in the order of 80° to 120° C., in order to obtain a reasonably high speed of reaction, a so-called "popcorn" polymerization readily takes place which, in a relatively short period of time, can result in the build-up of appreciable quantities of insoluble polymer which clog the reactor. This danger is particularly great when the reaction is carried out continuously in a tube reactor. The popcorn polymerization can be avoided to a large extent by utilizing lower reaction temperatures, however the speed of the reaction is then so low as to make the process economically impracticable.

It has been found that the popcorn polymerization cannot be efficiently inhibited by use of the usual stabilizing agents such as hydroquinone, hydroquinone monomethyl ether, p-nitrosophenol, induline or methylene blue. A search has therefore been made for special stabilizers to inhibit the popcorn polymerization. In U.S. Pat. No. 2,819,296 it was proposed to utilize alkali metal nitrites for this purpose. These are useful, however, only if the reaction mixture contains at least small quantities of water to bring the alkali nitrite into solution. Unfortunately, this water becomes bound to the alkylene oxide in the course of the reaction so that the activity of the inhibitor disappears. Continuous addition of small quantities of water is undesirable because the glycols that are formed due to reaction with water form impurities in the reaction product.

The use of nitric oxide $N_2O_2$ as a stabilizing agent for this reaction is suggested in British Patent No. 970,202 as well as in German Offenlegungschrift No. 1,618,260. The difficulty with this suggestion is that the nitric oxide gas must be used in a form practically free from nitrogen dioxide. Inasmuch as nitric oxide reacts very readily with the oxygen in air to form nitrogen dioxide, it is necessary to operate in an oxygen-free atmosphere when nitric oxide is used as a stabilizer, a serious operational disadvantage.

The use of p-nitrophenol as a stabilizer for acrylic monomers to inhibit popcorn polymerization has been reported in German Offenlegungschrift No. 1,493,316. This publication indicates that neither nitrophenol nor nitric oxide are particularly efficient as inhibitors and both give to the acrylic monomer an undesirable yellowish appearance. Whereas the conjugated polyenes that are suggested appear to have some stabilization efficacy in the distillation of acrylic monomers, they do not appear to have any significant stabilizing effect in the preparation of hydroxy esters of acrylic or methacrylic acid.

It has now been found that the popcorn polymerization which has heretofore plagued the preparation of hydroxy esters of acrylic and methacrylic acids by reaction of these acids with 1,2-alkylene oxides in the presence of basic catalysts can be avoided by carrying out the reaction in the presence of a compound having the formula $R-(NO_2)$, in which R is a linear or branched alkyl or alkenyl of from 1 to 18 carbon atoms. More particularly, these compounds which are effective as stabilizers include those having the structural formulae

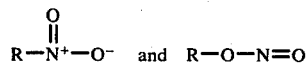

While all of the compounds represented by these formulae are operable and effective as inhibitors of popcorn polymerization, it should be noted that the nitrites of the latter formula in which R contains less than four carbon atoms are gaseous or highly volatile and are injurious to health. Thus, while they are basically operable, they should not be used in the process of this invention. Organic nitrogen compounds that have been found particularly useful in the method of this invention include nitromethane, nitropropane, nitrodecane, n-butyl nitrite, i-amyl nitrite and octadecyl nitrite.

The nitric acid esters, i.e., the nitrites, are effective as popcorn polymerization inhibitors in concentrations as low as 0.01% by weight based on the weight of acrylic or methacrylic acid reactant. The other stabilizing organic nitrogen compounds, such as nitromethane, nitropropane and the like should be present in quantities of at least about 0.05% by weight based on the weight of acrylic or methacrylic acid. In any event there is no need to include any more than a maximum of about 5% by weight of either type of organic nitrogen compound as stabilizer. The preferred concentration of stabilizer is in the range of from about 0.1 to 2% by weight of the acrylic or methacrylic acid reactant. The simultaneous presence of other well known polymerization inhibitors which are effective during distillation and storage of the ester monomers has no adverse effect on the stabilization activity of the organic nitrogen compounds.

The stabilizers used in the method of the invention are suitable for reaction of acrylic and methacrylic acids with various vicinal oxides, e.g. alkylene oxides such as ethylene oxide, propylene oxide, epichlorohydrin, butylene oxide, as well as such vicinal alkaryl oxides as styrene oxide, preferably at reaction temperatures of the order of from 80° to 120° C. at atmospheric or super atmospheric pressure up to for example, about 10 atmospheres. A particular advantage of the method of this invention is that the reaction can be carried out continuously in a tube reactor without incurring the difficulty of having it clogged by undesired polymerization products.

The catalysts that are useful in the process of this invention are the known basic nitrogen compounds such as triethylamine, tributylamine, N,N-dimethylaminoethanol, N,N-dimethylaniline, m-dimethylaminophenol and, more generally, tertiary amines containing three alkyl or hydroxyalkyl radicals of from 1 to 4 carbon atoms or two such radicals and a phenyl of hydroxyphenyl radical.

The vicinal oxides that are preferred as reactants with the acrylic acid or methacrylic acid in accordance with the method of this invention are those of the formula

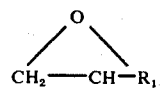

in which $R_1$ is hydrogen, methyl, chloromethyl, ethyl or phenyl.

The method of this invention will be further illustrated by the following examples:

EXAMPLE 1

A mixture of 1000 g/hr acrylic acid, 1050 g/hr propylene oxide, 37 g/hr N,N-dimethylaminoethanol, 10 g/hr nitromethane and 1 g/hr hydroquinone was continuously passed through, at a temperature of 90° C., a tube bundle reactor of stainless steel having a volume of 1 liter and an inside diameter of the tubes of 24 mm. The test was carried out for a total of 8 hours at a pressure of 10 atmospheres.

After separation of the excess epoxide, the crude ester mixture had, by gas chromatogram, a content of 90.5% 2-hydroxypropylacrylate and a diester content of 0.7%.

No polymer was found in the reactor.

EXAMPLE 2

A mixture of 930 g/hr methacrylic acid, 640 g/hr ethylene oxide, 28.8 g/hr N,N-dimethylaminoethanol, 18.6 g/hr nitromethane and 0.93 g/hr hydroquinone were passed through the apparatus described in Example 1 at a temperature of 90° C. and a pressure of 5 atmospheres. Acid number determination showed that 98% of the methacrylic acid was converted. The content of 2-hydroxyethyl methacrylate in crude ethylene oxidefree ester was 92.5%.

After proceeding in this manner for 8 hours, no polymer could be found in the reactor.

EXAMPLE 3

2-hydroxypropyl methacrylate was prepared in the same apparatus and in the same manner as described in Example 1 by reaction of a mixture of 1000 g/hr methacrylic acid, 887 g/hr propylene oxide, 37 g/hr N,N-dimethylaminoethanol, 5 g/hr nitromethane and 1 g/hr hydroquinone at a temperature of 100° C.

After 26 hours of continuous operation, the reactor was free of polymer.

Analysis of the crude ester showed a content of approximately 94% hydroxy ester.

EXAMPLE 4

The process of Example 1 was repeated with a mixture of 1000 g/hr methacrylic acid, 887 g/hr propylene oxide, 50 g/hr dimethylaniline, 2 g/hr nitropropane and 1 g/hr hydroquinone with approximately the same result.

EXAMPLE 5

A mixture of 720 g/hr acrylic acid, 572 g/hr ethylene oxide, 26.7 g/hr N,N-dimethylaminoethanol and 7.2 g/hr i-amyl nitrite were passed continuously through the apparatus described in Example 1 at a temperature of 90° C. and a pressure of from 5 to 10 atmospheres. The continuous process was carried out for 8 hours.

Samples of the crude ester showed a content of 85% 2-hydroxyethyl acrylate with a 96% conversion of acid. The reactor was completely free of polymers.

EXAMPLE 6

A mixture of 720 g/hr acrylic acid, 730 g/hr propylene oxide, 28.8 g/hr N,N-dimethylaminoethanol and 7.2 g/hr i-amyl nitrite were passed continuously through the apparatus described in Example 1 at 100° C. in the manner described in Example 5. This process was continued for 8 hours and at a pressure of 10 atmospheres.

After separation of the excess epoxide, the crude ester mixture contained, by gas chromatogram, a content of 87% 2-hydroxypropyl acrylate. The content of propane diol-1,2-diacrylate was 0.58%. There was no polymer in the reactor.

EXAMPLE 7

A mixture of 930 g/hr methacrylic acid (containing 50 ppm hydroquinone), 640 g/hr ethylene oxide, 28.8 g/hr dimethylaminoethanol and 9.3 g/hr i-amyl nitrite was continuously passed through the apparatus described in Example 1 at a temperature of 90° C. and a pressure of 5 to 6 atmospheres. After 8 hours, no polymer was in the apparatus. The content of 2-hydroxyethyl methacrylate was 92% in the ethylene oxidefree crude ester after an acid conversion of 96%.

EXAMPLE 8

2-hydroxypropyl methacrylate was prepared in the same apparatus and under the same reaction conditions as described in Example 5 by reacting, hourly, a mixture of 930 g methacrylic acid, 830 g proplyene oxide, 28.8 g N,N-dimethylaminoethanol, 9.3 g i-amyl nitrite and 0.93 g hydroquinone at a temperature of 100° C. After 8 hours of continuous operation, the reactor was free of polymer.

Analysis of the crude ester showed that a 97% acid conversion was obtained and that the content of hydroxy ester was 93%.

EXAMPLE 9

2-hydroxypropyl methacrylate was prepared as described in Example 8, the only difference being that 45 g N,N-dimethylamino-m-phenol were used as catalyst instead of N,N-dimethylaminoethanol.

The reactor was free of polymer after 8 hours of continuous operation. The concentration of 2-hydroxypropyl methacrylate in the crude ester was 93 to 94%. The acid conversion was 97.5%.

EXAMPLE 10

A mixture of 930 g/hr methacrylic acid (containing 50 ppm hydroquinone), 640 g/hr ethylene oxide, 28.8 g dimethylaminoethanol and 9 g n-butyl nitrite were continuously passed through the apparatus and under the conditions described in Example 5 at 90° C. No polymer was to be found in the reactor after 8 hours of operation.

EXAMPLE 11

A mixture of 720 g/hr acrylic acid, 730 g/hr propylene oxide, 28.8 g/hr N,N-dimethylaminoethanol and 7.2 g/hr 1-nitrodecane were passed continuously through the apparatus described in Example 1 at 100° C. at a pressure of 10 atmospheres for a period of 8 hours.

After separation of the excess epoxide, the crude ester mixture contained, according to gas chromatogram, a content of 88% 2-hydroxypropyl acrylate. The propane diole-1,2-diacrylate concentration was 0.73%.

The reactor was free of polymer.

EXAMPLE 12

A mixture of 930 g/hr methacrylic acid (containing 50 ppm hydroquinone), 640 g/hr ethylene oxide, 28.8 g/hr dimethylaminoethanol and 9 g/hr octadecyl nitrite was continuously passed through the reactor described in Example 1 at 90° C. in the manner described in Example 5. After 8 hours, the reactor was still completely free of polymer.

EXAMPLE 13

To a mixture of 172 g of methacrylic acid, 5.3 g of N,N-dimethylamino ethanol, 1.72 g of iso-amylnitrit, and 0.086 g of hydroquinone, in a reaction flask, 250 g of styrene oxyde were added dropwise at 100° C. After 5 hours, a conversion of 90 percent of the methacrylic acid was obtained. The reaction flask was free of polymer.

We claim:

1. In a process for preparing a hydroxy ester of acrylic or methacrylic acid which comprises reacting a vicinal alkylene oxide or styryl oxide with acrylic or methacrylic acid in the presence of a basic nitrogen compound, the improvement which comprises carrying out the reaction in the presence of up to about 5% by weight, based on the weight of acrylic or methacrylic acid, of a compound of the formula $$R-(NO_2)$$

as stabilizer, in which R is a linear or branched alkyl or alkenyl of from 1 to 18 carbon atoms.

2. The process defined in claim 1 in which R is a linear or branched alkyl of 1 to 18 carbon atoms.
3. The process defined in claim 1 in which the stabilizer is nitromethane.
4. The process defined in claim 1 in which the stabilizer is nitropropane.
5. The process defined in claim 1 in which the stabilizer is nitrodecane.
6. The process defined in claim 1 in which the stabilizer is n-butyl nitrite.
7. The process defined in claim 1 in which the stabilizer is i-amyl nitrite.
8. The process defined in claim 1 in which the stabilizer is octadecyl nitrite.
9. The process defined in claim 1 in which the stabilizer is present in a concentration of from about 0.1 to about 2% by weight.
10. The process defined in claim 1 in which vicinal alkylene oxide is a compound of the formula

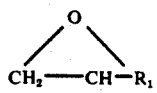

in which $R_1$ is H, $CH_3$, $CH_2Cl$, $C_2H_5$ or phenyl.

11. The process defined in claim 1 in which the reaction is carried out continuously at a temperature between about 80° and 120° C.

* * * * *